(12) United States Patent
Breitinger et al.

(10) Patent No.: US 10,398,106 B1
(45) Date of Patent: Sep. 3, 2019

(54) DISEASE RESISTANCE ALLELES IN SOYBEAN

(71) Applicant: Syngenta Participations AG, Basel (CH)

(72) Inventors: Becky Welsh Breitinger, Research Triangle Park, NC (US); Thomas Joseph Curley, Jr., Research Triangle Park, NC (US); Anderson Rotter Meda, Londrina-PR (BR); Flavia Fernandes Carneiro, Uberlândia (BR)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 15/797,382

(22) Filed: Oct. 30, 2017

Related U.S. Application Data

(60) Provisional application No. 62/415,661, filed on Nov. 1, 2016.

(51) Int. Cl.
*A01H 5/10* (2018.01)
*C12Q 1/6876* (2018.01)
*A01H 1/02* (2006.01)

(52) U.S. Cl.
CPC ............... *A01H 5/10* (2013.01); *A01H 1/02* (2013.01); *C12Q 1/6876* (2013.01); *C12Q 2600/13* (2013.01)

(58) Field of Classification Search
None
See application file for complete search history.

(56) References Cited

PUBLICATIONS

Funke et al., 1993, Plant Molecular Biology 22: 437-446, published Dec. 2, 2008.*
Funke et al., 1993, Plant Molecular Biology 22: 437-446.*
Kang et al. Genome-wide mapping of NBS-LBR genes and their association with disease resistance in soybean. BMC Plant Biology 2012 12:139.
Dong et al. Fine mapping of a resistance gene to bacterial leaf pustule in soybean. Theor. Appl . Genet (2010) 120:1443-1450.
Kil et al. Marker-assisted foreground and background selection of near isogenic lines for bacterial leaf pustule resistant gene in soybean. J. Crop Sci. Biotech. Dec. 2008 11(4): pp. 263-268.
Hao-Xun et al. Characterization of disease resistance loci in the USDA soybean germplasm collection using genome-wide association studies. Genetics and Resistance vol. 106, No. 10 2016 pp. 1139-1151.

* cited by examiner

*Primary Examiner* — Bratislav Stankovic
(74) *Attorney, Agent, or Firm* — Amy Krom

(57) ABSTRACT

The present invention relates to methods and compositions for identifying, selecting and/or producing a soybean plants having increased resistance to bacterial pustule disease. A soybean plant or germplasm that has been identified, selected and/or produced by any of the methods of the present invention is also provided. Disease resistant soybean seeds, plants and germplasms are also provided.

6 Claims, No Drawings
Specification includes a Sequence Listing.

US 10,398,106 B1

DISEASE RESISTANCE ALLELES IN SOYBEAN

CROSS REFERENCES TO RELATED APPLICATIONS

The presently disclosed subject matter claims the benefit of U.S. Provisional Patent Application Ser. No. 62/415,661, filed Nov. 1, 2016 which is herein incorporated by reference in its entirety.

STATEMENT REGARDING ELECTRONIC FILING OF A SEQUENCE LISTING

A Sequence Listing in ASCII text format, submitted under 37 C.F.R. § 1.821, entitled 81114_ST25.txt, 16,384 bytes in size, generated on Oct. 28, 2016 and filed via EFS-Web, is provided in lieu of a paper copy. This Sequence Listing is hereby incorporated by reference into the specification for its disclosures.

FIELD OF THE INVENTION

The present invention relates to compositions and methods for identifying, selecting and/or producing soybean plants having tolerance to soybean bacterial pustule.

BACKGROUND

Soybean (*Glycine max* L. Merr) is a major cash crop and investment commodity in North America and elsewhere. Soybean oil is one of the most widely used edible oils, and soybeans are used worldwide both in animal feed and in human food production. Bacterial pustule, caused by *Xanthomonas axonopodis* pv. glycines (Xag), is a serious bacterial disease of soybean. Bacterial pustule is widespread in many soybean-growing regions of the world where high temperature and humidity prevail. It is a foliar disease of soybean, with symptoms typically occurring on leaves that include small, pale green spots with elevates pustules, which may develop into large necrotic lesion causing premature defoliation. Bacterial pustule resistance is controlled by a single recessive gene rxp (resistance to *Xanthomonas axonopodis*). However, two QTL regions were reported in the literature, one was mapped at 3.9 cM from Satt372 and 12.4 cM from Satt014 on linkage group D2 and another mapped at 129.3 cM (Satt108) at LG O. The present invention relates to a newly identified QTL region associated to bacterial pustule resistance at LG C2.

Different varieties of soybean vary in their sensitivity or tolerance to bacterial pustule. Therefore, one of the most effective control measures is planting bacterial pustule tolerant soybean varieties, and thus varietal selection is important for the management of bacterial pustule. However, currently, determining whether a soybean cultivar might have tolerance to bacterial pustule typically involves testing each cultivar in the field or greenhouse under conditions that typically produce bacterial pustule. Thus, the present invention overcomes the shortcomings in the art by providing markers associated with tolerance to bacterial pustule using a novel loci, thereby allowing the characterization of soybean cultivars for bacterial pustule by molecular analysis rather than phenotypic analysis.

Until now bacterial pustule resistance has only been assessed through phenotyping, which can be time consuming and can only be done at late stages of breeding programs, due to its low throughput. This invention describes the discovery of a new QTL region in the soybean genome that is associated with resistance to this pathogen. The ultimate benefit of this invention is to select resistant progenies based on SNP markers at early breeding stages and support the breeding pipeline by filling it in with lines enriched for the resistance allele.

Further, the invention provides a novel loci and/or chromosome interval corresponding to *Glycine max* chromosome 6 making it possible to select and/or produce commercial soybean plants having increased resistance to bacterial pustule.

SNP markers associated with bacterial pustule resistance in soybean will support selections by the soybean breeding programs on earlier breeding stages and will assure that only plants with desirable (resistance) alleles will be advanced to late stage testing. Also, there is an expected improvement of cost efficiency by eliminating the need of expensive low throughput phenotyping at early breeding stages, thus increasing accuracy of the selection and maximizing the value of investments in field testing. From a trait introgression perspective, the SNP marker can be deployed for rapid introgression of both GM and native traits; expansion of allele frequency for native traits in a broad germplasm base.

SUMMARY OF THE INVENTION

Compositions and methods for identifying, selecting and producing soybean plants having bacterial pustule resistance alleles are provided. Soybean plants and/or soybean germplasms and/or parts thereof having bacterial pustule resistance/tolerance alleles are also provided.

Accordingly, in one aspect of the invention one may use a marker within a chromosomal interval corresponding to soybean chromosome 6 to select, identify or produce soybean lines having increased resistance/tolerance to bacterial pustule. Specifically, a marker selected from a chromosomal interval defined as 20 cM, 10 cM or 5 cM from any marker identified in Table 1 or corresponding to SEQ ID Nos: 1-7. In another embodiment the chromosomal interval is from about 49,139,963 to about 49,974,519 (Herein 'BP Chromosomal interval') wherein the interval comprises any one of a molecular marker that associates with bacterial pustule resistance wherein the interval that comprises a marker corresponding to a A at position 1295 of SEQ ID NO: 1; a A at position 308 of SEQ ID NO: 2; a G at position 61 of SEQ ID NO: 3; a A at position 251 of SEQ ID NO: 4; a T at position 251 of SEQ ID NO: 5; a A at position 251 of SEQ ID NO: 6; and a T at position 273 of SEQ ID NO: 7.

A further aspect of the invention provides a method of introgression of a bacterial pustule resistance allele into a soybean germplasm that is lacking the said resistance allele, the method comprising: (a) crossing a donor parental soybean line comprising a genetic marker associated with an bacterial pustule resistance allele with a recurrent parental soybean line that lacks said genetic marker to produce a progeny plant; (b) selecting a progeny plant comprising said marker and backcrossing said progeny plant with a recurrent parental soybean line, wherein said progeny plant is selected by detecting, in its genome the presence of said genetic marker on a chromosome interval corresponding to soybean chromosome 6 at positions 49,139,963 to 49,974,519 and further wherein the interval comprises the following alleles corresponding to a A at position 1295 of SEQ ID NO: 1; a A at position 308 of SEQ ID NO: 2; a G at position 61 of SEQ ID NO: 3; a A at position 251 of SEQ ID NO: 4; a T at position 251 of SEQ ID NO: 5; a A at position 251 of SEQ ID NO: 6; and a T at position 273 of SEQ ID NO: 7.

Compositions comprising a primer pair capable of amplifying a nucleic acid sample isolated from a maize plant or germplasm to generate a marker associated with a bacterial pustule resistance allele are also provided. Such compositions may comprise, consist essentially of or consist of one of the amplification primer pairs and/or probes as identified in Table 1.

These and other aspects of the invention are set forth in more detail in the description of the invention below Definitions Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP, QTL, haplotype) can mean one marker or a plurality of markers (e.g., 2, 3, 4, 5, 6, and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with tolerance to bacterial pustule in a soybean plant relative to a control soybean plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with a bacterial pustule tolerance allele" refers to a marker whose presence or absence can be used to predict whether a plant will display tolerance to bacterial pustule.

As used herein, the term "bacterial pustule resistance" or "bacterial pustule tolerance" refers to a plant's ability to endure and/or thrive despite being exposed to growth conditions in which bacterial pustule, e low as compared to one or more control plants (e.g., a plant lacking a marker associated with bacterial pustule.

Thus, "tolerance" in a soybean plant to bacterial pustule conditions is an indication that the soybean plant is less affected by the bacterial pustule conditions with respect to yield, survivability and/or other relevant agronomic measures, compared to a less tolerant, more "susceptible" plant. Tolerance is a relative term, indicating that a "tolerant" soybean plant survives and/or produces a better yield in bacterial pustule growth conditions when compared to a different (less tolerant) soybean plant (e.g., a different soybean strain or variety) grown in similar conditions bacterial pustule. That is, under bacterial pustule growth conditions a tolerant plant can have a greater survival rate and/or yield, as compared to a soybean plant that is susceptible or intolerant to these bacterial pustule growth conditions. Bacterial pustule "tolerance" sometimes can be used interchangeably with bacterial pustule "resistance." Bacterial pustule intolerant soybean varieties and cultivars are well known in the art.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example, in* TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding, in* PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with bacterial pustule tolerance may be introgressed from a donor into a recurrent parent that is bacterial pustule intolerant. The resulting offspring could then be backcrossed one or more times and selected until the progeny possess the genetic marker(s) associated with bacterial pustule tolerance in the recurrent parent background.

As used herein, the term "linkage" refers to the degree with which one marker locus is associated with another marker locus or some other. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., bacterial pustule. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of soybean genetic markers are known in the art, and are published or available from various sources, such as the SoyBase internet resource (soybase.org). In some embodiments, a genetic marker of this invention is an SNP allele, a SNP allele located in a chromosome interval and/or a haplotype (combination of SNP alleles) each of which is associated with bacterial pustule tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 1)

Accordingly, in some embodiments of this invention, a marker is detected by amplifying a *Glycine* sp. nucleic acid with two oligonucleotide primers by, for example, the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Non-limiting examples of probes of this invention include those listed in Table 1.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

As used herein, the term "probe" refers to a single-stranded oligonucleotide sequence that will form a hydrogen-bonded duplex with a complementary sequence in a target nucleic acid sequence analyte or its cDNA derivative.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence BLAST®X can be used to determine sequence identity; and for polynucleotide sequence BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "soybean" refers to a plant, and any part thereof, of the genus *Glycine* including, but not limited to *Glycine* max.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny", "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "reference sequence" refers to a defined nucleotide sequence used as a basis for nucleotide sequence comparison. The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the

DETAILED DESCRIPTION

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

Disclosed herein is the identification and design of genetic markers (SNPs and/or combinations of SNPs) that can be used to identify alleles associated with bacterial pustule resistance in soybean.

Therefore, the present invention provides compositions and methods for identifying, selecting and/or producing soybean plants having one or more bacterial pustule resistance alleles. In addition, the present invention provides soybean plants and/or soybean germplasm having within their genomes one or more SNP markers associated with one or more bacterial pustule resistance alleles. These SNPs are located within an approximately 0.8 megabase (MB) region of *Glycine* sp. Chromosome 6 (Linkage Group C2).

Genetic Mapping

Genetic loci correlating with particular phenotypes, such as resistance to bacterial pustule, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with bacterial pustule resistance alleles and thus, associated with resistance to particular races of bacterial pustule. Detection of these markers and/or other linked markers can be used to identify, select and/or produce plants having bacterial pustule resistance alleles, and thus, having resistance to bacterial pustule and/or to eliminate plants from breeding programs or from planting that do not have a bacterial pustule resistance allele and are not resistant to bacterial pustule.

Markers Associated with Tolerance to Bacterial Pustule

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

The recombination frequencies of genetic markers on different chromosomes and/or in different linkage groups are generally 50%. Between genetic markers located on the same chromosome or in the same linkage group, the recombination frequency generally depends on the physical distance between the markers on a chromosome. A low recombination frequency typically corresponds to a low genetic distance between markers on a chromosome. Comparison of all recombination frequencies among a set of genetic markers results in the most logical order of the genetic markers on the chromosomes or in the linkage groups. This most logical order can be depicted in a linkage map. A group of adjacent or contiguous markers on the linkage map that is associated with an increased level of resistance to a disease (e.g., to a reduced incidence of acquiring the disease upon infectious contact with the disease agent and/or a reduced lesion growth rate upon establishment of infection) can provide the position of a locus associated with resistance to that disease. The present invention provides SNP markers and/or combination of SNP markers that can be used in various aspects of the presently disclosed subject matter as set forth herein.

Thus, the SNP markers provided herein can be used for detecting the presence of one or more bacterial pustule resistance alleles in a soybean plant or germplasm, and can therefore be used in methods involving marker-assisted breeding and selection of bacterial pustule-resistant soybean plants/soybean plants having one or more bacterial pustule resistance alleles within a chromosomal interval corresponding to soybean chromosome 6 at positions 49,139,963 to 49,974,519 and/or comprising SNPs that associate with bacterial pustule resistance wherein said SNPs are any one of: a A at position 1295 of SEQ ID NO: 1; a A at position 308 of SEQ ID NO: 2; a G at position 61 of SEQ ID NO: 3; a A at position 251 of SEQ ID NO: 4; a T at position 251 of SEQ ID NO: 5; a A at position 251 of SEQ ID NO: 6; and a T at position 273 of SEQ ID NO: 7.

In some embodiments, methods for detecting the presence of an SNP in a soybean plant or germplasm can comprise providing a oligonucleotide or polynucleotide capable of hybridizing under stringent hybridization conditions to a nucleotide sequence of a SNP disclosed herein, contacting the oligonucleotide or polynucleotide with genomic nucleic acid (or a fragment thereof, including, but not limited to a restriction fragment thereof) of the soybean plant or germplasm, and determining the presence of the SNP by the specific hybridization of the oligonucleotide or polynucleotide to the soybean genomic nucleic acid (or the fragment thereof).

Table 1 provides information about the bacterial pustule associated markers presented including the physical location of the marker on the respective soybean chromosome, and the target allele that is associated with bacterial pustule. Markers of the present invention are described herein with respect to the positions of marker loci in the 8x public build of the Williams82 soybean genome at the SoyBase internet resource (soybase.org/SequenceIntro.php) or USDA at (bf-gl.anri.barc.usda.gov/cgi-bin/soybean/Linkage.pl). See Table 1 below.

TABLE 1

Description of the SNP markers associated with bacterial pustule resistance

| Ref. Sequence | Name | Marker Sequence (SEQ ID NO) (location of allele) | Position in Reference Sequence | Marker Alleles Favorable Allele | Unfavorable Allele | Amplification Primer Pair (SEQ ID NO) | Marker Probes (SEQ ID NO) |
|---|---|---|---|---|---|---|---|
| Glycine max L. cultivar Williams 82 (Gm06) | SY0770AQ | 1 (nt 1295) | 49,974,519 | A | C | 8/9 | 10/11 |
| | SY0980AQ | 2 (nt 308) | 49,897,408 | A | G | 12/13 | 14/15 |
| | SY1292AQ | 3 (nt 61) | 49,329,146 | G | A | 16/17 | 18/19 |
| | SY1872AQ | 4 (nt 251) | 49,139,963 | A | G | 20/21 | 22/23 |
| | SY1873AQ | 5 (nt 251) | 49,207689 | T | A | 24/25 | 26/27 |
| | SY1874AQ | 6 (nt 251) | 49,266,653 | A | G | 28/29 | 30/31 |
| | SY2872 | 7 (nt 273) | 49,897,679 | T | A | 32/33 | 34/35 |

In further embodiments, a marker of this invention can include any marker linked to the aforementioned markers as described in Table 1. Linked markers may be determined, for example, by using resources available on the SoyBase internet resource (soybase.org).

The presently disclosed subject matter thus also relates to methods for identifying, selecting, and/or producing soybean plants having an bacterial pustule resistance allele comprising detecting in a donor soybean plant the presence of a genetic marker associated with an bacterial pustule resistance allele and/or a genetic marker associated with bacterial pustule resistance as described herein and transferring the nucleotide sequence comprising the at least one genetic marker thus detected from the donor soybean plant to a bacterial pustule-recipient soybean plant. It is noted that the recipient soybean plant can be resistant to certain bacterial pustule races and susceptible to other bacterial pustule races. Typically, the recipient soybean plant is at least susceptible to the race of bacterial pustule for which the transfer of the nucleotide sequence comprising the genetic marker (associated with a bacterial pustule resistance allele) confers resistance (transferred from the donor soybean plant). In other embodiments, the recipient soybean plant can susceptible to all bacterial pustule races. This allows the breeder to develop soybean plants having resistance to one or more races of bacterial pustule. The transfer of the nucleotide sequence can be performed by any of the methods described herein.

Thus, methods for identifying, selecting and/or producing a soybean plant or germplasm comprising a bacterial pustule resistance allele can comprise detecting the presence of a genetic marker associated with a bacterial pustule resistance allele. The SNP marker can be detected in any sample taken from the soybean plant or germplasm, including, but not limited to, the whole plant or germplasm, a portion of said plant or germplasm (e.g., a cell, leaf, seed, etc., from said plant or germplasm) or a nucleotide sequence from said plant or germplasm.

As discussed herein, in some embodiments of this invention, a marker can be identified using amplification products generated by amplifying a Glycine sp. nucleic acid with two oligonucleotide primers. In some embodiments, the amplification is by PCR, and the primers are PCR primers that are designed to hybridize to opposite strands of the Glycine sp. genomic DNA in order to amplify a Glycine sp. genomic DNA sequence present between the sequences to which the PCR primers hybridize in the Glycine sp. genomic DNA. Methods of amplifying nucleic acids are well known in the art.

Accordingly, in some embodiments of the present invention, a method of identifying and/or selecting a soybean plant or germplasm having an bacterial pustule resistance allele is provided, the method comprising: detecting, in said soybean plant or germplasm, the presence of a genetic marker associated with the bacterial pustule resistance allele, wherein said marker is detected in amplification products from a nucleic acid sample isolated from said soybean plant or germplasm using a probe, said amplification products having been produced using pairs of amplification primers wherein said amplification primers and probes as described in Table 1.

Marker-Assisted Selection

The subject matter disclosed herein also relates to methods for producing pathogen-resistant soybean plants comprising detecting the presence of a genetic marker associated with pathogen resistance in a donor soybean plant according to the methods as described herein and transferring a nucleic acid sequence comprising at least one genetic marker thus detected from the donor plant to a recipient soybean plant. The transfer of the nucleic acid sequence can be performed by any method known in the art.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus Glycine having bacterial pustule resistance comprising detecting in the plant the presence of one or more bacterial pustule resistance alleles as defined herein. In an exemplary embodiment of the presently disclosed methods for selecting such a plant, the method comprises providing a sample of genomic DNA from a soybean plant; and (b) detecting in the sample of genomic DNA at least one genetic marker associated with bacterial pustule resistance. In some embodiments, the detecting comprises detecting one or more SNPs that are associated with bacterial pustule resistance. Samples of genomic DNA from a soybean plant can be performed by standard DNA isolation methods well known in the art.

The detecting of a genetic marker (e.g., SNP, combination of SNPs) can in some embodiments comprise the use of one or more sets of primer pairs (SNP assays) that can be used to produce one or more amplification products that can be used in the detection of genetic markers (SNPs). Such a set of primers can comprise, in some embodiments, nucleotide sequences as set forth in Table 1.

In some embodiments, the detecting of a genetic marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker. In some embodiments, the detecting of a genetic marker is designed to determine whether a particular allele of a SNP is present or absent in a particular plant.

The presently disclosed subject matter thus also relates to methods for producing pathogen-resistant soybean plants comprising detecting the presence of a genetic marker associated with an Bacterial pustule resistance allele (or a genetic marker associated with bacterial pustule resistance) in a donor soybean plant according to the presently disclosed subject matter as described herein and transferring a nucleotide sequence comprising at least one genetic marker thus detected, or a bacterial pustule resistance-conferring part thereof, from the donor plant to a recipient soybean plant. In particular embodiments, the recipient soybean plant is susceptible to the race of bacterial pustule for which said transferred nucleotide sequence confers resistance. The transfer of the nucleic acid sequence can be performed by any of the methods described herein.

An exemplary embodiment of the invention comprises the transfer of the nucleic acid sequence from a pathogen-resistant donor soybean plant into a recipient soybean plant by crossing the plants by introgression. This transfer can be accomplished by using traditional breeding techniques. Pathogen-resistance loci are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode for the desired trait. As disclosed herein, such identification and selection is based on selection of SNP alleles of this invention or markers associated therewith. MAB can also be used to develop near-isogenic lines (NIL) comprising one or more pathogen resistant alleles of interest, allowing a more detailed study of an effect of such allele(s). MAB is also an effective method for development of backcross inbred line (BIL) populations. Soybean plants developed according to these embodiments can in some embodiments derive a majority of their traits from the recipient plant, and derive pathogen resistance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with pathogen resistance into a recipient soybean plant. The recipient soybean plant may be resistant or susceptible to one or more pathogens or to one or more bacterial pustule races. In some embodiments of the present invention, the recipient soybean plant is susceptible to the Bacterial pustule race for which resistance is conferred by transferring said nucleic acid sequence associated with pathogen resistance. Thus, for example, inbred pathogen-resistant soybean plant lines can be developed using the techniques of recurrent selection and backcrossing, selfing, and/or di-haploids, or any other technique used to make parental lines. In a method of recurrent selection and backcrossing, pathogen resistance can be introgressed into a target recipient plant (the recurrent parent) by crossing the recurrent parent with a first donor plant, which differs from the recurrent parent (i.e., non-recurrent parent). The recurrent parent is a plant that is non-resistant or has a low level of resistance to one or more pathogens or to a particular race of a pathogen but, in some embodiments, possesses commercially desirable characteristics, such as, but not limited to (additional) disease and/or insect resistance, valuable nutritional characteristics, valuable abiotic stress tolerance (including, but not limited to, drought tolerance, salt tolerance), and the like. In some embodiments, the non-recurrent parent exhibits pathogen resistance and comprises a nucleic acid sequence that is associated with pathogen resistance (e.g., increased resistance to bacterial pustule). The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding, for example, bacterial pustule resistance or a genetic marker associated with Bacterial pustule resistance (e.g., SNPs and SNP combinations described herein). Also, MAB can be used to confirm the results obtained from the quantitative bioassays. In some embodiments, the markers defined herein are suitable to select proper offspring plants by genotypic screening.

Following screening, F1 hybrid plants that exhibit a pathogen-resistant phenotype or, in some embodiments, the genotype, and thus comprise the requisite nucleic acid sequence associated with pathogen resistance, are then selected and backcrossed to the recurrent parent in order to allow for the soybean plant to become increasingly inbred. The process of selecting and backcrossing can be repeated for a number of generations (e.g., for one, two, three, four, five, six, seven, eight, or more generations).

Thus, a marker that demonstrates linkage with a locus affecting a desired phenotypic trait provides a useful tool for selection of the trait in a plant population. This is particularly true where the phenotype is difficult to assay or occurs at a late stage in plant development. Since marker assays are less laborious and take up less physical space than field phenotyping, much larger populations can be assayed, increasing the chances of finding a recombinant plant with the target segment from the donor line that is moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the soybean genome containing increasing densities of public soybean markers has facilitated soybean genetic mapping and MAS. See, e.g. soybeanbreederstoolbox.org, which can be found on the SoyBase internet resource (soybase.org).

Of the types of genetic marker available, SNPs are some of the most abundant and have the potential to provide the highest genetic map resolution (Bhattramakki et al., Plant Molec. Biol. 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, mini-sequencing and coded spheres. Such methods have been reviewed in various publications: Gut, Hum. Mutat. 17:475 (2001); Shi, Clin. Chem. 47:164 (2001); Kwok, Pharmacogenomics 1:95 (2000); Bhattramakki and Rafalski, Discovery and application of single nucleotide polymorphism markers in plants, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Soybean Plants, Parts Thereof, and Germplasms Having Bacterial Pustule Resistance Alleles The present invention provides soybean plants and germplasms having bacterial pustule resistance alleles and resistance to bacterial pustule. As discussed above, the methods of the present invention can be utilized to identify, produce and/or select a soybean plant or germplasm having a bacterial pustule resistance allele. In addition to the methods described above, a soybean plant or germplasm having an bacterial pustule resistance allele may be produced by any method whereby a marker associated with an bacterial pustule resistance allele is introduced into the soybean plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, micro-particle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system. It is further contemplated that recent genome editing tools can be used to modify a non-resistant soybean germplasm to having bacterial pustule resistance by changing its genomic DNA to correspond with the bacterial resistance alleles as described in Table 1.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having a bacterial pustule resistance allele (i.e., bacterial pustule-resistant soybean plant or part thereof), obtainable by the methods of the presently disclosed subject matter, are aspects of the presently disclosed subject matter. In some embodiments, the soybean plant of the present invention has more than one bacterial pustule resistance allele as described herein.

The soybean plant, or part thereof, of this invention having a bacterial pustule resistance allele can be heterozygous or homozygous for the resistance allele. In some embodiments of this invention, the soybean plant has more than one bacterial pustule resistance allele and thus, can be heterozygous at some bacterial pustule resistance alleles and homozygous at other bacterial pustule resistance alleles.

The soybean plant or germplasm may be the progeny of a cross between a variety of soybean and a second variety of soybean that comprises a bacterial pustule resistance allele.

The soybean plant or germplasm may be the progeny of an introgression wherein the recurrent parent is a variety of soybean and the donor comprises a bacterial pustule resistance allele.

The soybean plant or germplasm may be the progeny of a cross between a first variety of soybean (e.g., a tester line) and the progeny of a cross between a second variety of soybean (e.g., a recurrent parent) and a variety of soybean that comprises an bacterial pustule resistance allele (e.g., a donor).

The soybean plant or germplasm may be the progeny of a cross between a first variety of soybean and the progeny of an introgression wherein the recurrent parent is a second variety of soybean and the donor comprises a bacterial pustule resistance allele.

Another aspect of the presently disclosed subject matter relates to a method of producing seeds that can be grown into bacterial pustule-resistant soybean plants. In some embodiments, the method comprises providing a bacterial pustule-resistant soybean plant of this invention, crossing the bacterial pustule-resistant plant with another soybean plant, and collecting seeds resulting from the cross, which when planted, produce bacterial pustule-resistant soybean plants.

Accordingly, the present invention provides improved soybean plants, seeds, and/or tissue cultures produced by the methods described herein. In further embodiments, the present invention provides introgressed *Glycine max* plants and/or germplasm produced by the methods described herein.

Compositions for Analysis of a Soybean Genome

In some embodiments, the presently disclosed subject matter provides methods for analyzing the genomes of soybean plants/germplasms to identify those that include desired markers associated with Bacterial pustule resistance.

In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs capable of initiating DNA polymerization by a DNA polymerase on a *Glycine max* nucleic acid template to generate a *Glycine max* marker amplicon. In some embodiments, the *Glycine max* amplicon can be used to identify the *Glycine max* marker comprising a nucleotide sequence of any of SEQ ID NOs: 1-7. In view of the disclosure of SEQ ID NOs: 1-7 as being linked to pathogen resistance loci, one of ordinary skill in the art would be aware of various techniques that could be employed to analyze the sequences of the corresponding soybean nucleic acids. Representative amplification primer pairs can comprise the nucleotide sequences of a forward primer and corresponding reverse primer as set forth hereinabove in Table 1.

That which is claimed:

1. A method of producing a soybean plant having increased resistance to bacterial pustule, the method comprising the steps of:
   a. isolating a nucleic acid from a soybean plant part;
   b. detecting in the nucleic acid of a) at least one molecular marker that is associated with increased bacterial pustule resistance, wherein said molecular marker is localized within 1 cM of an allele corresponding to:
      an A at position 308 of SEQ ID NO: 2;
   c. selecting or identifying a soybean plant on the basis of the presence of said molecular marker of b);
   d. crossing the soybean plant of c) with a second soybean plant not comprising the molecular marker of b); and
   e. producing progeny plant from the cross of d) thereby, producing a soybean plant having increased resistance to bacterial pustule.

2. The method of claim 1, wherein the marker is located within a chromosome interval corresponding to *Glycine max* chromosome 6 between and including physical positions 49139963 to 49974519.

3. The method of claim 1, wherein detecting comprises: a) admixing an amplification primer or amplification primer pair with a nucleic acid isolated from a soybean plant or soybean germplasm, wherein the primer or primer pair is complementary or partially complementary to at least a portion of the marker locus, and is capable of initiating DNA polymerization by a DNA polymerase using the soybean nucleic acid as a template; and, b) extending the primer or primer pair in a DNA polymerization reaction comprising a DNA polymerase and a template nucleic acid to generate at least one informative fragment wherein the informative fragment comprises SEQ ID NO: 2.

4. The method of claim 1, wherein the progeny plant is an elite soybean plant.

5. The method of claim 3, wherein the primer pair comprises SEQ ID NO pair: 12 and 13.

6. The method of claim 1, wherein the molecular marker is a single nucleotide polymorphism (SNP), a quantitative trait locus (QTL), an amplified fragment length polymorphism (AFLP), randomly amplified polymorphic DNA (RAPD), a restriction fragment length polymorphism (RFLP) or a microsatellite.

* * * * *

SEQUENCE LISTING

```
<160> NUMBER OF SEQ ID NOS: 35

<210> SEQ ID NO 1
<211> LENGTH: 1624
<212> TYPE: DNA
<213> ORGANISM: Glycine max
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t

<400> SEQUENCE: 1
gagaaattat tctctaacaa gcaaaattcg aaaattcttt tccctttaaa agggtaatgc      60
cctatacaac ctgcaattcc aaacctgtat gctcattgct attagcagaa gaagaggttt     120
caggatgttc cttgtcatca gtagacttca tctcttgaac gggaggagca tttacaatgg     180
ttgtctcaga gaaaatactg tcagaaagcc ttcctttcat ctccctgtgc tcttgacaca     240
aggcacacca gtgcatgcag cagtgcacac aacatggatc acatggtgag ttctgcagtc     300
atcaaaagat tgagtgagaa aatcttaaca gcaaaacaag gtttatgtgc tgggaaaacc     360
ataaaagcta aaggagaaaa agaaaattga aatgttactt gtgtgtttgg tttgacttgc     420
tttggagaaa aaaatgcttc ttttattgtg ccagcttaat gagatttaga ggaaaaaatg     480
agatgcaaaa cagtgcaatg tacacaaagg caccaaagca aggcaaggtg tgtgcgtgcc     540
tctggctaag gcaaggcaca tctctaacat ctcatcagta ttagtcaaac tgnaaaaccc     600
agtcatctaa cttagtgaat gagacactaa agaaagtaac atggcctgaa tgttaaaaga     660
ataacagttt ttggtttttc cgactttag cagcagcagc cagcaagcag cttaggattt      720 catcaaattga atatcataat cttttattta tatacgaatg aaatgtttag tagtaaattt     780
atgaaaaaca tgaaaatagt caatatattt ctatttcttt tttaatacta atgccatgtt     840
tttttaggaa aactgatgtc tttttgtact gaaatgctta gcatgcactt tcgccccaag     900
tcattaagcc acttggcatt ttaagggtgc ctttcctttt actacattga aacattgata     960
gcattagcta tttttttccc tctcctctgt ataggtattg gaaagagat ggcaacaaca     1020 aagtttaagt aaatttgata agttttaaca gaatatttat tgtgtattat tgcttcaatt    1080
tccggctaaa ggtcntttcc taataatgag gacagcattc tagagttctt ttattctcgt    1140
taccagacta gtagtttttc aatcactaaa aatttatctt gtaagaaaac atcatttctc    1200
aaactacatg gttggtttaa aactgttgac atttgatgcc agacttgctg aaagttcgtg    1260
tttcaattca ccaagaataa cactagaatc atgtacatac attcatttat caggttttca    1320
ttgttagatt acagaccatc aagtatatct tcatatctat ttcattcaaa gttgttcaaa    1380
atatgcatgt acggttccag tcaaaaaggt cttactagtt actatgtcag atgagtattt    1440
```

-continued

```
gatatataca gattcctaca caaaggagat ttttttttaa catataatga aatctacatt    1500
acacatttgc aataagaaga agcattattt cacggcagat gagtatttga tacgcgcgcg    1560
cgcgcacaca caaaaagata tactattcca tccttaaagt ttactagtcc aagtgaaaag    1620
atat                                                                1624

<210> SEQ ID NO 2
<211> LENGTH: 742
<212> TYPE: DNA
<213> ORGANISM: Glycine max
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 2
ttctacctga attgatatac tcagattgca ccctttttag gcatttctaa gtatttacaa      60
cttgccctgg tccttcctct ttatcaagtt gaaaagtgtt tgctacacgc tttctaacat     120
actattttta acacactcta ttattagcta aaatttattg gaaacaacaa aatcatgagt     180
ggagattcat caaataagga gtgagacgca caattttgtt attctcaatg attcttggcc     240
aataataaat aaagtgttta taagagtatg ctngaaagtg cattgctacc atttctctta     300
ccaggttata tccttatatg gcgtagtctt gtgataaatt tcttatcttt cattctcact     360
tctaacatca tcatataatt tagaggaata atatcncaat ttacctgatt attgcattca     420
caacattgtt ttactgtaga ttggttaatt ttaataggaa aaatgttaaa ttgggactac     480
cttcattcag atggagcaat caatacagtt atgacatgca tatttgtgag cacaagagtg     540 atttttagatg tgttaataat ttcaatctga tgttaaggaa gaattttttn atatactcat    600
atacccatag ttaaattgat ctccttgtac ctttcttgga atatttgttc agagactaaa    660
tatatattat catttctttt tctattgctt agctccccat gtcttgtggg aatcacttat    720
ttgttaaaag catgatgtga tt                                             742

<210> SEQ ID NO 3
<211> LENGTH: 121
<212> TYPE: DNA
<213> ORGANISM: Glycine max
<220> FEATURE:
<221> NAME/KEY: misc_feature
<222> LOCATION: (50)..(50)
<223> OTHER INFORMATION: n is a, c, g, or t

<400> SEQUENCE: 3
agattcatta ataaaaacag aaaagcatat acaagagatg aaagcaaaan actctaacaa      60
ggggattgtc caaggctgga cgtagattct gaacctaaaa ttaggtaaag aaaatttatt     120
t                                                                    121

<210> SEQ ID NO 4
<211> LENGTH: 501
<212> TYPE: DNA
<213> ORGANISM: Glycine max
<220> FEATURE:
<221> NAME/KEY: misc_feature
```

<222> LOCATION: (240)..(240)
<223> OTHER INFORMATION: n is a, c, g, or t

<400> SEQUENCE: 4

| | | | | |
|---|---|---|---|---|
| cttcagagat | tttagccatc | ctacctggat | atcctgacaa | tgtgagagtc | aatgaagatg | 60 |
| gtgattttg | ggtagctctt | cattctagaa | ggtatatgta | tgcatactac | aatggtatct | 120 |
| acccaaagat | gaggaaaata | atactcaagc | ttcctatacc | aataaagatt | cattacctgc | 180 |
| ttcaaatcgg | gggtcgccaa | cacgcagcgg | ttatcaggta | tagccctgaa | ggtaaacttn | 240 |
| tgcagatttt | agaggacagt | gaggggaaag | ttgttaaagc | agtgagtgaa | gtggaggaga | 300 |
| aggatggtaa | actttggatg | ggaagtgttc | tcatgccttt | tgttgcagta | tacaacttga | 360 |
| aatgatgccg | atgattagat | gattctcccc | caccaaggat | ctattttttt | cttttctatc | 420 |
| ttgaattggc | cagttgaaga | agttgaattt | tgattcaaca | ttatcaataa | tggaccttaa | 480 |
| cttcctggtt | gaaaatcctg | a | | | | 501 |

<210> SEQ ID NO 5
<211> LENGTH: 501
<212> TYPE: DNA
<213> ORGANISM: Glycine max

<400> SEQUENCE: 5

| | | | | | | |
|---|---|---|---|---|---|---|
| gaaggtgaaa | tctaaaattg | ttaagaaatc | tcaaactgtt | aaacttaagg | ccaagaagaa | 60 |
| aaatggttct | caacaaattt | gtgggaaaag | agttatgagt | tcaaagaag | tggtggacaa | 120 |
| ttctgaaaat | tgtcacattg | cagatgagaa | acaaatttca | gacgatagtg | agctgaagga | 180 |
| aactaatgat | gagccaccta | aggggaagag | tgaagaggct | gaaaataaaa | tgaaaggtag | 240 |
| tcaaaataca | tgcaccggta | acaaaagtcc | tattgaagag | ttagatggta | tccaactgaa | 300 |
| ggatactgat | cctcctgaag | gatttagtaa | acctgagttg | agtgacaaga | atactctaaa | 360 |
| atcattgaag | gaaaattcta | acattgttaa | gaaatctcaa | gctgttaaag | ttaaggccaa | 420 |
| gaagtaccat | ggttctcaac | aagttcatgg | gaaaaaaaga | attgtgactt | caaaaaaagt | 480 |
| ggtggacaat | gctgaaagtt | g | | | | 501 |

<210> SEQ ID NO 6
<211> LENGTH: 501
<212> TYPE: DNA
<213> ORGANISM: Glycine max
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t

<400> SEQUENCE: 6

| | | | | | | |
|---|---|---|---|---|---|---|
| aacgttttg | tcatccctaa | tcattctgtt | ttttgtcatc | cctaatcatt | ctgtgtgtta | 60 |
| ttgatctcct | ttcaatgtcc | aaaaaacgtt | acatgatttg | aaaccccaac | aacaccgatg | 120 |
| gcttgttttc | acgaactaat | aattcaaaac | caacacaatg | tagtgcttaa | cactatgaag | 180 |
| caatgaaaac | caaattaata | aaaaaaatag | cacaaataaa | accaaactct | aatttgatga | 240 |
| tgggcatgca | actaacattc | aacaccaaaa | caacagcaaa | atgtcacatt | tacatcctct | 300 |

```
gatactcccg aaaatttaag ggcactatat attattaaga aactttctca ctctcccaat    360
acatgcaaat taacaatttt ttttgganag gccacacctg gtcattaaaa gagactatcc    420
tacntgagtc gactagttca gtagaactac taanattgta ggcaacaaac aaagttcttc    480
gtccaactct gagactagga a                                              501
```

```
<210> SEQ ID NO 7
<211> LENGTH: 742
<212> TYPE: DNA
<213> ORGANISM: Glycine max
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 7
```

```
ttctacctga attgatatac tcagattgca ccctttttag gcatttctaa gtatttacaa     60
cttgccctgg tccttcctct ttatcaagtt gaaaagtgtt tgctacacgc tttctaacat    120
actattttta acacactcta ttattagcta aaatttattg gaaacaacaa atcatgagt    180 ggagattcat caaataagga gtgagacgca caattttgtt attctcaatg attcttggcc    240
aataataaat aaagtgttta taagagtatg cttgaaagtg cattgctacc atttctctta    300
ccaggttnta tccttatatg gcgtagtctt gtgataaatt tcttatcttt cattctcact    360
tctaacatca tcatataatt tagaggaata atatcncaat ttacctgatt attgcattca    420
caacattgtt ttactgtaga ttggttaatt ttaataggaa aaatgttaaa ttgggactac    480
cttcattcag atggagcaat caatacagtt atgacatgca tatttgtgag cacaagagtg    540
attttagatg tgttaataat ttcaatctga tgttaaggaa gaattttttn atatactcat    600
atacccatag ttaaattgat ctccttgtac ctttcttgga atatttgttc agagactaaa    660
tatatattat catttctttt tctattgctt agctccccat gtcttgtggg aatcacttat    720
ttgttaaaag catgatgtga tt                                             742
```

```
<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gttcgtgttt caattcacc                                                  19
```

```
<210> SEQ ID NO 9
<211> LENGTH: 22
<212> TYPE: DNA
<213> ORGANISM: Artificial Sequence
<220> FEATURE:
<223> OTHER INFORMATION: PRIMER

<400> SEQUENCE: 9
gatggtctgt aatctaacaa tg                                              22
```

```
<210> SEQ ID NO 10
<211> LENGTH: 19
<212> TYPE: DNA
<213> ORGANISM: Artificial Sequence
<220> FEATURE:
<223> OTHER INFORMATION: PROBE

<400> SEQUENCE: 10
aacactagaa tcatgtaca                                              19

<210> SEQ ID NO 11
<211> LENGTH: 18
<212> TYPE: DNA
<213> ORGANISM: Artificial Sequence
<220> FEATURE:
<223> OTHER INFORMATION: PROBE

<400> SEQUENCE: 11
cactagaatc atgtccat                                               18

<210> SEQ ID NO 12
<211> LENGTH: 19
<212> TYPE: DNA
<213> ORGANISM: Artificial Sequence
<220> FEATURE:
<223> OTHER INFORMATION: PRIMER

<400> SEQUENCE: 12
gaaagtgcat tgctaccat                                              19

<210> SEQ ID NO 13
<211> LENGTH: 17
<212> TYPE: DNA
<213> ORGANISM: Artificial Sequence
<220> FEATURE:
<223> OTHER INFORMATION: PRIMER

<400> SEQUENCE: 13
cacaagacta cgccata                                                17

<210> SEQ ID NO 14
<211> LENGTH: 17
<212> TYPE: DNA
<213> ORGANISM: Artificial Sequence
<220> FEATURE:
<223> OTHER INFORMATION: PROBE

<400> SEQUENCE: 14
cttaccaggt tatatcc                                                17

<210> SEQ ID NO 15
<211> LENGTH: 16
<212> TYPE: DNA
<213> ORGANISM: Artificial Sequence
<220> FEATURE:
<223> OTHER INFORMATION: PROBE

<400> SEQUENCE: 15
ttaccaggtt gtatcc                                                 16

<210> SEQ ID NO 16
<211> LENGTH: 17
<212> TYPE: DNA
<213> ORGANISM: Artificial Sequence
<220> FEATURE:
<223> OTHER INFORMATION: PRIMER
```

<400> SEQUENCE: 16
gaatctacgt ccagcct                                                      17

<210> SEQ ID NO 17
<211> LENGTH: 21
<212> TYPE: DNA
<213> ORGANISM: Artificial Sequence
<220> FEATURE:
<223> OTHER INFORMATION: PRIMER

<400> SEQUENCE: 17
gcatatacaa gagatgaaag c                                                 21

<210> SEQ ID NO 18
<211> LENGTH: 15
<212> TYPE: DNA
<213> ORGANISM: Artificial Sequence
<220> FEATURE:
<223> OTHER INFORMATION: PROBE

<400> SEQUENCE: 18
tggacaatcc ccttg                                                        15

<210> SEQ ID NO 19
<211> LENGTH: 16
<212> TYPE: DNA
<213> ORGANISM: Artificial Sequence
<220> FEATURE:
<223> OTHER INFORMATION: PROBE

<400> SEQUENCE: 19
tggacaatcc ctttgt                                                       16

<210> SEQ ID NO 20
<211> LENGTH: 25
<212> TYPE: DNA
<213> ORGANISM: Artificial Sequence
<220> FEATURE:
<223> OTHER INFORMATION: PRIMER

<400> SEQUENCE: 20
tcactcactg ctttaacaac tttcc                                             25

<210> SEQ ID NO 21
<211> LENGTH: 20
<212> TYPE: DNA
<213> ORGANISM: Artificial Sequence
<220> FEATURE:
<223> OTHER INFORMATION: PRIMER

<400> SEQUENCE: 21
caacacgcag cggttatcag                                                   20

<210> SEQ ID NO 22
<211> LENGTH: 15
<212> TYPE: DNA
<213> ORGANISM: Artificial Sequence
<220> FEATURE:
<223> OTHER INFORMATION: PROBE

<400> SEQUENCE: 22
cactgtcctc caaaa                                                        15

<210> SEQ ID NO 23
<211> LENGTH: 16

```
<212> TYPE: DNA
<213> ORGANISM: Artificial Sequence
<220> FEATURE:
<223> OTHER INFORMATION: PROBE

<400> SEQUENCE: 23
ctcactgtcc tctaaa                                                        16

<210> SEQ ID NO 24
<211> LENGTH: 17
<212> TYPE: DNA
<213> ORGANISM: Artificial Sequence
<220> FEATURE:
<223> OTHER INFORMATION: PRIMER

<400> SEQUENCE: 24
ggaagagtga agaggct                                                       17

<210> SEQ ID NO 25
<211> LENGTH: 18
<212> TYPE: DNA
<213> ORGANISM: Artificial Sequence
<220> FEATURE:
<223> OTHER INFORMATION: PRIMER

<400> SEQUENCE: 25
ccttcaggag gatcagta                                                      18

<210> SEQ ID NO 26
<211> LENGTH: 18
<212> TYPE: DNA
<213> ORGANISM: Artificial Sequence
<220> FEATURE:
<223> OTHER INFORMATION: PROBE

<400> SEQUENCE: 26
tagtcaaaat acaagcac                                                      18

<210> SEQ ID NO 27
<211> LENGTH: 18
<212> TYPE: DNA
<213> ORGANISM: Artificial Sequence
<220> FEATURE:
<223> OTHER INFORMATION: PROBE

<400> SEQUENCE: 27
tagtcaaaat acatgcac                                                      18

<210> SEQ ID NO 28
<211> LENGTH: 20
<212> TYPE: DNA
<213> ORGANISM: Artificial Sequence
<220> FEATURE:
<223> OTHER INFORMATION: PRIMER

<400> SEQUENCE: 28
tcagaggatg taaatgtgac                                                    20

<210> SEQ ID NO 29
<211> LENGTH: 19
<212> TYPE: DNA
<213> ORGANISM: Artificial Sequence
<220> FEATURE:
<223> OTHER INFORMATION: PRIMER

<400> SEQUENCE: 29
```

```
ccaacacaat gtagtgctt                                                    19
```

```
<210> SEQ ID NO 30
<211> LENGTH: 17
<212> TYPE: DNA
<213> ORGANISM: Artificial Sequence
<220> FEATURE:
<223> OTHER INFORMATION: PROBE

<400> SEQUENCE: 30
tgttgaatgt tagctgc                                                      17
```

```
<210> SEQ ID NO 31
<211> LENGTH: 18
<212> TYPE: DNA
<213> ORGANISM: Artificial Sequence
<220> FEATURE:
<223> OTHER INFORMATION: PROBE

<400> SEQUENCE: 31
tgttgaatgt tagttgca                                                     18
```

```
<210> SEQ ID NO 32
<211> LENGTH: 24
<212> TYPE: DNA
<213> ORGANISM: Artificial Sequence
<220> FEATURE:
<223> OTHER INFORMATION: PRIMER

<400> SEQUENCE: 32
tcaaataagg agtgagacgc acaa                                              24
```

```
<210> SEQ ID NO 33
<211> LENGTH: 25
<212> TYPE: DNA
<213> ORGANISM: Artificial Sequence
<220> FEATURE:
<223> OTHER INFORMATION: PRIMER

<400> SEQUENCE: 33
atcacaagac tacgccatat aagga                                             25
```

```
<210> SEQ ID NO 34
<211> LENGTH: 17
<212> TYPE: DNA
<213> ORGANISM: Artificial Sequence
<220> FEATURE:
<223> OTHER INFORMATION: PROBE

<400> SEQUENCE: 34
agcaatgcac tttcaag                                                      17
```

```
<210> SEQ ID NO 35
<211> LENGTH: 18
<212> TYPE: DNA
<213> ORGANISM: Artificial Sequence
<220> FEATURE:
<223> OTHER INFORMATION: PROBE

<400> SEQUENCE: 35
tagcaatgca ctttctag                                                     18
```